US011759134B2

United States Patent
Macknik et al.

(10) Patent No.: US 11,759,134 B2
(45) Date of Patent: *Sep. 19, 2023

(54) SYSTEMS AND METHODS FOR NON-INTRUSIVE DECEPTION DETECTION

(71) Applicants: Dignity Health, San Francisco, CA (US); Arizona Board of Regents on behalf of Arizona State University, Scottsdale, AZ (US)

(72) Inventors: Stephen L. Macknik, Anthem, AZ (US); Susana Martinez-Conde, Anthem, AZ (US); Richard E. Dale, Scottsdale, AZ (US); Richard Besserman, Phoenix, AZ (US); Troy Lee McDaniel, Chandler, AZ (US)

(73) Assignee: ARIZONA BOARD OF REGENTS ON BEHALF OF ARIZONA STATE UNIVERSITY DIGNITY HEALTH, Scottsdale, AZ (US)

( * ) Notice: Subject to any disclaimer, the term of this patent is extended or adjusted under 35 U.S.C. 154(b) by 467 days.

This patent is subject to a terminal disclaimer.

(21) Appl. No.: 16/994,403

(22) Filed: Aug. 14, 2020

(65) Prior Publication Data

US 2021/0059589 A1  Mar. 4, 2021

Related U.S. Application Data

(63) Continuation of application No. 15/317,339, filed as application No. PCT/US2015/035253 on Jun. 11, 2015, now Pat. No. 10,743,806.

(Continued)

(51) Int. Cl.
- *A61B 5/16* (2006.01)
- *A61B 3/113* (2006.01)
- *A61B 5/11* (2006.01)

(52) U.S. Cl.
CPC .............. *A61B 5/164* (2013.01); *A61B 3/113* (2013.01); *A61B 5/11* (2013.01)

(58) Field of Classification Search
CPC .......... A61B 3/113; A61B 5/163; A61B 5/164
See application file for complete search history.

(56) References Cited

U.S. PATENT DOCUMENTS

| 4,456,347 A | 6/1984 | Stahly |
| 4,815,839 A | 3/1989 | Waldorf |

(Continued)

FOREIGN PATENT DOCUMENTS

| CA | 2674542 | 10/2012 |
| CA | 2720962 | 6/2016 |

(Continued)

OTHER PUBLICATIONS

Applicant Initiated Interview Summary for U.S. Appl. No. 15/306,892 dated Jan. 30, 2019.

(Continued)

*Primary Examiner* — Kaylee R Wilson
*Assistant Examiner* — Raymond P Dulman
(74) *Attorney, Agent, or Firm* — Quarles & Brady LLP

(57) ABSTRACT

Systems and methods for detecting deceptive intent of a subject include observing eye movements of the subject and correlating the observed movements to known baseline neurophysiological indicators of deception. A detection system may record eye movement data from the subject, compare the eye movement data to a data model comprising threshold eye movement data samples, and from the comparison make a determination whether or not the subject is lying. The detection system may create an alert if deception is detected. The eye movements detected include saccadic and intersaccadic parameters such as intersaccadic drift velocity. Measurements may be collected in situ with a field (Continued)

testing device, such as a non-invasive, non-contact device attached to the subject's computing device and configured to non-obtrusively record the eye movement data.

13 Claims, 2 Drawing Sheets

Related U.S. Application Data

(60) Provisional application No. 62/010,658, filed on Jun. 11, 2014.

(56) References Cited

U.S. PATENT DOCUMENTS

| | | | |
|---|---|---|---|
| 5,137,345 A | | 8/1992 | Waldorf |
| 5,360,971 A | | 11/1994 | Kaufman |
| 5,382,989 A | | 1/1995 | Uomoroi |
| 5,422,690 A | | 6/1995 | Rothberg |
| 5,564,433 A | * | 10/1996 | Thornton ............ A61B 5/369 600/390 |
| 5,957,859 A | * | 9/1999 | Rosenfeld ............ A61B 5/164 128/898 |
| 6,120,461 A | | 9/2000 | Smyth |
| 7,027,621 B1 | | 4/2006 | Prokoski |
| 7,309,125 B2 | | 12/2007 | Pugach |
| 7,857,452 B2 | | 12/2010 | Martinez-Conde |
| 7,881,493 B1 | | 2/2011 | Edwards |
| 8,348,428 B2 | | 1/2013 | Martinez-Conde |
| 8,373,106 B2 | | 2/2013 | Macknik |
| 8,668,337 B2 | | 3/2014 | Waldorf |
| 8,721,081 B2 | | 5/2014 | Martinez-Conde |
| 8,808,179 B1 | | 8/2014 | Cinberg |
| 9,101,312 B2 | | 8/2015 | Waldorf |
| 9,123,050 B2 | | 9/2015 | Ryu |
| 9,301,679 B2 | | 4/2016 | Martinez-Conde |
| 9,763,573 B2 | | 9/2017 | Distasi |
| 9,962,119 B2 | | 5/2018 | Macknik |
| 10,231,166 B2 | | 3/2019 | Li |
| 10,231,617 B2 | | 3/2019 | Macknik |
| 10,791,926 B2 | | 10/2020 | Macknik |
| 11,013,441 B2 | | 5/2021 | Samadani |
| 2003/0028081 A1 | | 2/2003 | Blazey |
| 2004/0181168 A1 | | 9/2004 | Plant |
| 2005/0073136 A1 | | 4/2005 | Larsson |
| 2005/0128434 A1 | | 6/2005 | Tanchulev |
| 2005/0200808 A1 | | 9/2005 | Wyatt |
| 2006/0202841 A1 | | 9/2006 | Johns |
| 2007/0013868 A1 | | 1/2007 | Pugach |
| 2007/0017534 A1 | | 1/2007 | Thorpe |
| 2007/0132950 A1 | | 6/2007 | Victor |
| 2007/0265507 A1 | | 11/2007 | De Lemos |
| 2007/0273832 A1 | | 11/2007 | Weinblatt |
| 2008/0188777 A1 | | 8/2008 | Bedziouk |
| 2009/0198148 A1 | | 8/2009 | Lonky |
| 2009/0232357 A1 | | 9/2009 | Angell |
| 2009/0318773 A1 | | 12/2009 | Jung |
| 2010/0010370 A1 | | 1/2010 | De Lemos |
| 2010/0039617 A1 | | 2/2010 | Martinez-Conde |
| 2010/0094161 A1 | | 4/2010 | Kiderman |
| 2010/0100001 A1 | | 4/2010 | Aguilar |
| 2010/0191156 A1 | | 7/2010 | Sakamoto |
| 2010/0208205 A1 | | 8/2010 | Tseng |
| 2010/0277693 A1 | | 11/2010 | Martinez-Conde |
| 2010/0324454 A1 | | 12/2010 | Kircher |
| 2011/0109879 A1 | | 5/2011 | Palti-Wasserman |
| 2012/0081666 A1 | | 4/2012 | Kiderman |
| 2012/0182523 A1 | | 7/2012 | Wyatt |
| 2012/0238903 A1 | | 9/2012 | Martinez-Conde |
| 2013/0139258 A1 | | 5/2013 | Tegreene |
| 2013/0184781 A1 | | 7/2013 | Eskandar |
| 2013/0215390 A1 | | 8/2013 | Johns |
| 2013/0278899 A1 | | 10/2013 | Waldorf |
| 2013/0336547 A1 | | 12/2013 | Komogortsev |
| 2014/0114148 A1 | | 4/2014 | Shepherd |
| 2014/0114165 A1 | | 4/2014 | Walker |
| 2016/0019410 A1 | | 1/2016 | Komogortsev |
| 2016/0022137 A1 | | 1/2016 | Wetzel |
| 2016/0250355 A1 | | 9/2016 | Macknik |
| 2017/0000339 A1 | | 1/2017 | Di Statsi |
| 2017/0119296 A1 | | 5/2017 | Macknik |
| 2017/0131766 A1 | | 5/2017 | He |
| 2017/0135577 A1 | | 5/2017 | Komogortsev |
| 2017/0258368 A9 | | 9/2017 | Macknik |
| 2018/0116507 A1 | | 5/2018 | Otero-Millan |
| 2020/0022622 A1 | | 1/2020 | Macknik |
| 2020/0146611 A1 | | 5/2020 | Macknik |

FOREIGN PATENT DOCUMENTS

| | | |
|---|---|---|
| EP | 2490584 | 2/2019 |
| JP | H06154167 | 6/1994 |
| JP | 2001-309890 | 11/2001 |
| WO | 2010107568 | 9/2010 |
| WO | 2012103470 | 8/2012 |
| WO | 2013078461 | 5/2013 |
| WO | 2015051272 | 4/2015 |
| WO | 2015167992 | 11/2015 |

OTHER PUBLICATIONS

European Extended Search Report and written opinion for EP15806106, dated Jan. 23, 2018.
Extended European Search Report for Application 15786251.7, dated Dec. 15, 2017, 7 pages.
International Search Report & Written Opinion dated Jul. 24, 2015 in connection with PCT/JS2015/027730.
IP Australia Examination Report No. 1 for Application 2015253487, dated Mar. 15, 2019, 4 pages.
IP Australia Examination Report No. 1 for Application 2015274601, dated Feb. 19, 2019, 3 pages.
Office Action for U.S. Appl. No. 15/306,892 dated Jul. 23, 2018.
Office Action for U.S. Appl. No. 15/306,892 dated Nov. 13, 2018.
Written Opinion of the International Searching Authority dated Sep. 17, 2015 for International Application No. PCT/US2015/035253.
Benitez, J. T. "Eye-tracking and optokinetic tests: Diagnostic significance in peripheral and central vestibular disorders." The Laryngoscope 80.6 (1970): 834-848.
International Search Report dated Sep. 17, 2015 for International Application No. PCT/US2015/035253.
International Search Report and Written Opinion dated Sep. 29, 2014 in connection with PCT/US2014/35082.
Ziad M. Hafed et al., Microsaccades as an Overt Measure of Covert Attention Shifts, Vision Research 42 (2002) 2533-2545.
Japan Patent Office, Notification for Reason of Refusal for application 2019-065170. dated Apr. 21, 2020. With translation.
Martinez-Conde, S. et al. "Windows on the mind." Scientific American 297.2 (2007): 56-63.
PCT International Search Report and Written Opinion, PCT/US2015/046117, dated Nov. 19, 2015, 11 pages.
European Patent Office, Extended European Search Report, Application No. 15833830.1, dated Apr. 18, 2018, 9 pages.

* cited by examiner

```
                    ┌─────────────────┐
              ┌─ ─ ─│ Calibrate to User│◄─ ─ ─┐
┌──────────────┐   │└─────────────────┘       │
│Record Baseline│   │         │                │
│ Measurements │   115        ▼                │
└──────────────┘   │ ┌─────────────────┐       │
 100      │        │ │  Record In Situ │       │
          ▼        │ │ Measurements of │       │
┌──────────────┐   │ │     Subject     │       │
│Calculate Threshold│ └─────────────────┘       │
│ Drift Velocities │ 120      │                │
└──────────────┘            ▼                │
 105      │         ┌─────────────────┐       │
          ▼         │ Calculate Current│       │
┌──────────────┐    │  Drift Velocity │       │
│ Generate Data│    └─────────────────┘       │
│    Model     │    125      │                │ No
└──────────────┘             ▼                │
 110      │         ┌─────────────────┐       │
          └─ ─ ─ ─ ─│ Compare Current │       │
                    │ Drift Velocity to│       │
                    │   Data Model    │       │
                    └─────────────────┘       │
                    130      │                │
                             ▼                │
                           ╱ ╲                │
                          ╱Lying╲─────────────┘
                          ╲  ?  ╱
                           ╲ ╱
                            │ Yes
                            ▼
                    ┌─────────────────┐
                    │   Alert User    │
                    └─────────────────┘
                     135
```

FIG. 2

SYSTEMS AND METHODS FOR NON-INTRUSIVE DECEPTION DETECTION

CROSS-REFERENCE TO RELATED APPLICATIONS

This application is a continuation of, and claims the benefit of priority from, U.S. patent application Ser. No. 15/317,339, filed under the same title on Dec. 8, 2016, which is a National Stage application representing entry into the U.S. of International Application No. PCT/US2015/035253, filed under the same title on Jun. 11, 2015, and claiming the benefit of priority from U.S. Provisional Patent Application Ser. No. 62/010,658 filed Jun. 11, 2014, all of which applications are incorporated by reference herein in their entirety for all purposes.

BACKGROUND OF THE INVENTION

The present disclosure generally relates to systems and methods for acquiring data from a subject and, more particularly, to systems and methods for gathering and analyzing information about the subject's eye movements to identify deception by the subject without contacting the subject.

It is known that practicing lies and deceit provokes physiological changes in the lying subject. Physiological parameters that may deviate from normal when a subject is lying include blood pressure, pulse rate, respiration, and skin conductivity. Known "lie detector" technology can track these changes. In particular, a polygraph records and measures some of the changing physiological parameters of the subject while the subject is asked a series of questions. The underlying understanding about polygraphs is that deceptive answers are associated with autonomic-controlled physiologic responses of the subject person that can readily be differentiated from the physiological responses associated with non-deceptive answers.

Polygraphy, also known as a lie detector test, is used as an element of the process of providing "security clearance" for highly sensitive and trusted positions in industry, law enforcement, government, and critical infrastructure. Polygraphy is also used extensively in law enforcement as a screening tool to validate statements made by witnesses or suspects. This form of testing requires the presence of a highly trained, skilled operator to conduct an examination, perform an evaluation of the results, validate the findings, and report a conclusion. Even though polygraphy is typically inadmissible in a court of law, many law enforcement agencies believe that the results are accurate when the test is conducted by expert operators.

Polygraphy's main disadvantage is its reliance on measuring indirect physiologic responses that are evoked during a deceptive answer to a question. This is considered an indirect measure of autonomic response as opposed to a direct measure of brain activity. It is generally thought that observation of brain function may provide a better means of identifying deceptive behavior. Some have suggested making polygraphy more robust by adding additional measurements, such as facial thermography. Others have recommended direct measurements of brain function (e.g., EEG) or brain imaging (e.g., PET, MRI), but these suggestions have failed to represent practical advancements in the field. Finally, behavior measures have been suggested. They include demeanor, use of voice, facial expression, body movements, or choice of words. Such measures are subjective and rely upon experienced observers. A non-invasive, non-contact system that measures brain function to identify lies and deceit is needed.

Such a system could serve to identify lies and deceit even remotely, which would aid in a relatively new environment of dangerous deception: online interactions. The use of social media and other internet applications—for example, financial transactions and dating sites—has changed how people must rely upon the truthfulness of interpersonal communication. The public is at a far greater risk complicated by an even greater reliance of an unsuspecting user population. These Internet and web-based applications have virtually eliminated one-to-one contact in which participants can assess the truthfulness of another's statement, story, or claim. The visual and auditory clues we typically rely on have been replaced by user interfaces that rely on text, email, voicemail, and video communications. Truthful and reliable communications are important to users of dating sites and introductory services that rely almost entirely on the participants' representations. Likewise financial and other Internet service providers rely upon truthful responses from respondents. These new types of communication and changes in prior forms of communication expose the parties to the potential of deception, and the likelihood that one person may take advantage of another person's vulnerabilities and trust. A system that can protect users of these online services by identifying deception is needed.

SUMMARY OF THE INVENTION

The present invention overcomes drawbacks of previous technologies by providing systems and methods that afford a number of advantages and capabilities not contemplated by, recognized in, or possible in traditional system or known methodologies related to identifying when a test subject is lying or providing deceptive responses.

In one embodiment of the present invention, systems and methods are provided for monitoring, recording, and/or analyzing eye movements in situ to determine whether oculomotor dynamics are being affected by the subject's deceptive intent. In one aspect, a sensor arrangement may include a camera and recording assembly for detecting and recording the eye movements.

In some contemplated embodiments, systems and methods using in situ testing of eye movement dynamics may be employed to identify the onset or presence of abnormal eye movements as a result of the subject lying or otherwise attempting to deceive. Eye saccades and the velocity of intersaccadic eye drift are detectably affected by such deceit. A system and method may alert a user to the deceit in a testing environment. In particular, a system in accordance with the present invention may include devices and device assemblies that record baseline data of a subject and generate a data model representing the eye movement data of the subject, and further the system may include devices and device assemblies that record eye movement data in situ and compare it to the data model to determine if the subject is lying or being deceitful or deceptive.

In a contemplated embodiment of the present invention, a system includes a sensing arrangement that collects eye movement data of a subject, and a control unit in communication with the sensing arrangement. The control unit may be configured to compare the eye movement data to one or more baseline measurements of eye movement dynamics and, if the eye movement data diverges from one or more of the baseline measurements by a threshold amount, generate an alert for delivery to the subject. Comparing the eye movement data to the baseline measurements may include calculating a current intersaccadic drift velocity of the subject and comparing the current intersaccadic drift velocity to one or more threshold drift velocities of the baseline measurements. The eye movement data may include one or more saccade parameters, and comparing the eye movement data to the baseline measurements may include calculating a current intersaccadic drift velocity of the subject from the saccade parameters and comparing the current intersaccadic drift velocity to one or more threshold drift velocities of the baseline measurements. The baseline measurements may include one or more bio-signatures of a response condition. The response condition may be a deceptive answer or a truthful answer to a question.

In another embodiment of the present invention, a method of determining a physiological state of a subject includes recording from the subject eye movement data of one or both of the subject's eyes, comparing the eye movement data to one or more baseline measurements, and, if the eye movement data diverges from one or more of the baseline measurements by a threshold amount, delivering an alert to the subject. The eye movement data may include one or both of saccade parameters and intersaccadic drift parameters. The baseline measurements may include one or more bio-signatures of a response condition. The response condition may be a deceptive answer or a truthful answer to a question.

In another embodiment of the present invention, systems and methods of the present invention may be combined as a kit or apparatus, whose advantages and capabilities will be readily apparent from descriptions below.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present invention will hereafter be described with reference to the accompanying drawings, wherein like reference numerals denote like elements.

FIG. 2 is a flowchart illustrating a method for detecting lies and deception in accordance with the present invention.

DETAILED DESCRIPTION

Figure 1:
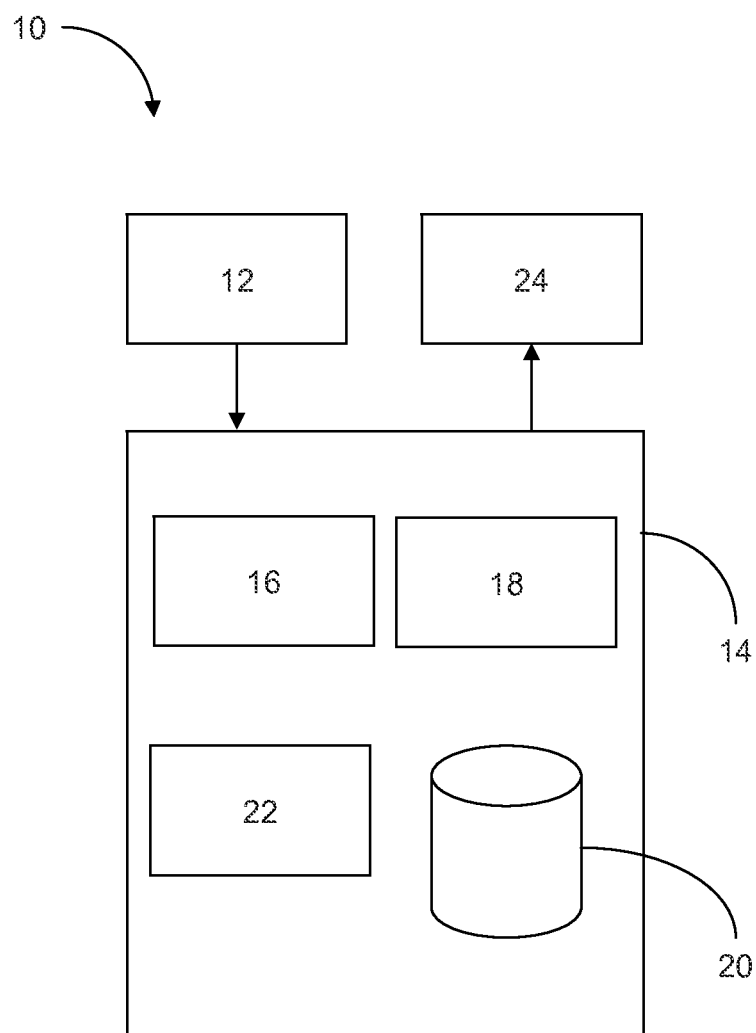
FIG. 1 is a diagram of a detection system in accordance with the present invention.

Systems and methods for detecting lies and deception through observation of eye movements are described herein. Deceptive intent or practice is shown by the inventors to affect oculomotor dynamics, including saccadic metrics and intersaccadic drift metrics. Select oculomotor dynamics can be tracked against a baseline to alert a subject that the subject is lying or attempting to deceive.

The systems and methods described herein are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims. For example, specific disclosure related to lie detection is provided, although it will be appreciated that the systems and methods may be applied for detection of other mental states without undue experimentation.

It is proposed herein that patterns of saccadic and micro-saccadic movement can be identified that are consistent with a subject's purposeful and deceptive answers to questions, or with other deceptive behavior. The present systems and methods analyze saccadic and micro-saccadic eye movements that are not under the control of the individual. The system eliminates dependence upon recording and measuring autonomic and physiologic responses as the primary means of determining whether the test subject and the answer is deceptive. Anatomically, a large portion of the human brain cortex is involved with the optic system that relies upon eye function for sensory awareness and survival. The invention described herein therefore analyzes the function of the brain more directly than known methods because it identifies, records, and analyzes eye movements that result from interaction between the centers of the brain that are responsible for eye tracking and those engaged with emotional and cognitive response.

Eye movement dynamics of the subject are readily identified, recorded, and analyzed by a measuring device to create a useful dataset for analysis. The dataset enables the comparison of eye movement responses associated with additional questions that may or may not be truthful. As other questions are asked, the eye movements are analyzed and compared to the baseline set to identify deception. The system performs additional complex analyses to build a dataset of analyzed eye movements that are characterized by their associated truthful or deceptive answers. The system thus provides a non-invasive, non-intrusive means to identify deception during an encounter or interview with a subject that is not dependent on measuring physiological responses. In particular, the system is ideally suited as a screening tool for internet, social media and other instances where people rely on others to be truthful and sincere.

Using the approach of the present invention, a detection system may record eye movement data from a subject, compare the eye movement data to a data model comprising threshold eye movement data samples, and from the comparison make a determination whether or not the subject's brain function is altered from a normal state due to the subject's attempt to lie to or deceive one or more individuals. The detection system may alert the test administrator or another party to the subject's deceit if an attempt is detected. The detection system does not require extensive training to use and is not prone to attempts by the subject to defeat the testing process by physiological duping.

Regarding the demonstrative eye movements, research has shown that certain neurologic conditions, such as diseases that affect the brain, can be identified and differentiated through the analysis of the test subject's saccadic and micro-saccadic eye movements. Saccadic and micro-saccadic eye movements are very closely tied to the measurement of brain function: As primary sensory organs, the eyes are extensions of the optic nerves, which are considered by many to be a part of the brain itself. The characteristic movements have been shown to be very consistent, and can be used to develop a bio-signature of a specific disease or condition. Measuring these eye movements may therefore be considered a more direct measurement of brain function than measurement of the physiological responses typically measured in polygraphy. Moreover, these eye movements can be analyzed to identify an attempt to deceive, as described herein.

Referring to FIG. 1, an embodiment of the detection system 10 may include a sensing arrangement 12 configured to detect and record eye movement dynamics of the subject. The sensing arrangement 12 may include one or more sensors suitable for collecting the eye movement data. Such sensors may include a camera or other imaging or motion tracking device capable of recording at a suitably high speed and level of detail so that the subject's eye movement dynamics, including saccades and intersaccadic drift, are captured. A monocular arrangement of one or more sensors for one of the subject's eyes may be used, or one or more sensors may be included for each eye to obtain binocular data. In some embodiments, the sensors may be miniaturized or otherwise compact, portable, and non-invasive. The sensors may further be vehicle-independent, and may be wireless, to facilitate integration of the sensors into any deployment of the detection system 10. For example, the sensing arrangement 12 may include sensors that are integrated into eyewear, such as on the frame or within the lenses of a pair of glasses. This allows for eye movement data collected even as the subject turns his head, and allows the sensors to be positioned close to the eyes. In another example, the sensors may be integrated into a "lie detector" testing device. In yet another example, the sensors may be integrated into existing personal devices, such as mobile phones and tablet computers. That is, the system 10 may use, as a sensor or array of sensors, the camera of the personal device in the sensing arrangement 12, and may use other native or add-on devices as well. In still another example, the system can be implemented over a social network, using data storage and processing on a service's servers, as well as laptops, webcams, and other devices of the social network's users as the components of the sensing arrangement 12.

The sensing arrangement 12 may further include integrated or discrete devices for processing, storing, and transmitting collected data. Such devices may include a processor, volatile and/or permanent memory, a wired or wireless transmitter, and associated power circuits and power supply for operating the devices. Software modules may define and execute instructions for operating the sensors, configuring databases, registers, or other data stores, and controlling transmission of the data. The collected data may be shared via transmission to a control unit 14 that may be integrated with or disposed physically remotely from the sensing arrangement 12. The eye movement data, or a subset thereof, may be transmitted in real-time as it is captured by the sensors, or it may be stored for later transmission.

The control unit 14 may use the processing hardware (i.e., processor, memory, and the like) of the sensing arrangement 12, or may include its own processing hardware for analyzing the eye movement data and generating an alert to the subject or other party if needed. The control unit 14 may include a plurality of modules that cooperate to process the eye movement data in a particular fashion, such as according to the methods described below. Each module may include software (or firmware) that, when executed, configures the control unit 14 to perform a desired function. A data analysis module 16 may extract information from the eye movement data for comparison to the data model. The data analysis module 16 may include one or more data filters, such as a Butterworth or other suitable bandpass filter, that retain only desired signal elements of the eye movement data. The data analysis module 16 may include program instructions for calculating, from the eye movement data, one or more eye movement dynamics, such as saccades and/or intersaccadic drift velocities, of the subject's eyes. The calculation may be performed substantially in real-time, such that a calculated intersaccadic drift velocity may be considered the current drift velocity of the subject's eyes.

A comparison module 18 may receive the processed eye movement data from the data analysis module 16 and may compare it to the data model as described in detail below. The control unit 14 may include or have access to a model data store 20 that stores the data model. The model data store 20 may be a database, data record, register, or other suitable arrangement for storing data. In some embodiments, the data model may simply be a threshold drift velocity, and may thus be stored as a single data record in memory accessible by the comparison module 18. In other embodiments, the data model may be a lookup table, linked list, array, or other suitable data type depending on the data samples for eye movement dynamics or bio-signatures needed to be stored in the data model.

In some embodiments, the control unit 14 may include a data model generator 22. The data model generator 22 is a module that receives eye movement data collected by the sensing arrangement 12 during a modeling step as described below. The data model generator 22 may extract, or cause the data analysis module 16 to extract, information from the collected eye movement data that will constitute the threshold eye movement data samples in the data model. The data model generator 22 may then create the data model from the threshold eye movement data samples, and may store the data model in the data model store 20. In other embodiments, the data model may be generated and stored in the data model store 20 by a separate modeling unit (not shown) of the system 10. The modeling unit may include its own sensing arrangement, processing hardware, and program modules. One suitable modeling unit may be the EyeLink 1000 by SR Research Ltd. of Mississauga, Ontario, Canada.

The control unit 14 may include or communicate with an alerting arrangement 24 configured to produce an alert to the subject, the subject's conversation partner, a test administrator, or another party, according to the results of the data comparison in the comparison module 18. The alerting arrangement may be any suitable indicator and associated hardware and software for driving the indicator. Suitable indicators present a visual, audible, or otherwise perceptible alert and include, without limitation: a visual display such as one or more light-emitting diodes, a liquid crystal display, a projector, a computer or mobile device screen, and the like; a bell, buzzer, or other audible signaling means; and a piezoelectric or other vibrating device. The alerting arrangement 24 may present the alert in the subject's vicinity, such as when the detection system 10 is used in a test environment. Additionally or alternatively, the alerting arrangement 24 may transmit the alert to a remote location immediately upon detecting the deceptive intent or at some later time.

In exemplary embodiments, the detection system 10 can be implemented to detect when a user is lying to a recipient of transmitted data, such as in a recorded video or audio clip, a phone call, a video or text chat, an email or other text-based message, and the like. The detection system 10 can alert the recipient to the deception as appropriate for the type of data transmission. In non-limiting examples, the alerting arrangement 24 can produce: during a phone call, an audio alert to the recipient via the phone when a lie is detected; in an email, a textual or graphical alert identifying the text being typed by the user when a lie was detected; in a video chat, a graphical alert on the recipient's screen when a lie is detected; and the like.

The detection system 10 may be used to execute any suitable method of detecting a deception by the subject that is indicated by eye movement data. FIG. 2, illustrates an example method of detecting the deception that can be performed by the system of FIG. 1. At step 100, the system may record baseline measurements of the eye movement dynamics for the data model. The baseline measurements are taken of an individual which may or may not be the subject. It may be advantageous that the data model use baseline measurements of the subject himself in order to individualize the operation of the system, but the baseline measurements may be taken from individuals other than the subject, or taken from a plurality of subjects and averaged if desired. The conditions in which the baseline measurements are recorded may depend on the desired specificity of the data model. In some embodiments, the baseline measurements may be taken in "normal conditions" by asking the subject non-threatening questions that have known answers, such that the test administrator is certain the subject is telling the truth. In other embodiments, the baseline measurements may be taken in known "deceptive conditions," wherein the subject is asked questions while under mental fatigue or duress. For example, the subject may be asked extremely difficult or subjective questions that induce changes in the eye movement dynamics. The baseline measurements may include eye movement parameters, including saccadic and microsaccadic movement, pupillary response, and eye response to light stimuli. The baseline measurements may also include eye measurements not directly related to movements, such as pupil size.

At step 105, the system may calculate one or more threshold drift velocities from the recorded baseline measurements. The threshold drift velocities may depend on the format of the collected baseline measurements. For example, where only normal-condition or only deceptive-condition baseline measurements were taken, a single threshold drift velocity (i.e., threshold-normal or threshold-deceptive drift velocity) may be calculated. Calculating the threshold drift velocities may include averaging calculated velocities from all or a portion of the individuals measured for baseline measurements. Similarly to calculation of drift velocities, any other measured parameter (e.g. pupil size or papillary response) may be calculated by averaging or normalizing the recorded baseline measurements from multiple individuals. At step 110, the system may generate the data model for the baseline-tested subject(s). The data model may represent the progression of the intersaccadic drift velocity of the subject from normal conditions to deceptive conditions. The data model may be generated and stored in any suitable format that allows the system to subsequently compare eye movement data collected in situ from the subject against the data model to determine whether the subject is lying.

The data model may include one or more bio-signatures of normal and/or deceptive responses. A bio-signature is a characteristic pattern that can be identified in measurements. This pattern is indicative of a state of stress or arousal, which may be absent when the subject is truthful and present when the subject is lying. The pattern may be evident by comparing the measurements of lying individuals to those of truthful individuals, or by comparing the measurements of a particular subject under deceptive conditions (i.e., when a response is known to be untruthful) to the subject's baseline measurements taken under normal conditions. In some embodiments, the bio-signatures may be synthesized from the baseline measurements. The bio-signatures may be general (i.e., standardized across a population of patients, such as by demographic) or patient-specific.

The steps 100, 105, 110 for obtaining the data model may be performed at any suitable time before testing the subject in situ for signs of deception. In one embodiment, the steps 100-110 may be performed far in advance and remotely from the test environment. In another embodiment, the steps 100-110 may be performed in the test environment, immediately preceding testing the subject. For example, the subject may activate the system 10, such as by donning and activating eyewear housing the sensing assembly 12, which initiates step 100 of recording the baseline measurements in the present conditions. This may be in normal conditions, wherein the test administrator asks simple questions such as "what is your name?" In still other embodiments, the data model may be created by the system 10 or another system using a different method than described above.

At step 115, optionally the system may calibrate itself to the subject if the data model or comparison method require it. For example, the data model may be a standardized model generated from baseline measurements of (an) individual(s) other than the subject, or the comparison method may determine the presence of deception from a percentage deviation from the subject's threshold-normal drift velocity value(s). In such an embodiment, the system calibrates (step 115) by recording a calibration set, such as ten seconds or less but preferably five seconds or less, of eye movement data of the subject when the system is activated in the test environment under normal conditions. The system may compare the calibration data to the data model. In one embodiment, this involves determining a deviation of the subject's threshold-normal drift velocity from the threshold-normal drift velocity of the model. The system can then adapt the data model to the subject.

At step 120, the system may record in situ eye movement data from the subject continuously or at predetermined intervals while the system is activated. At step 125, the system may calculate, in real-time or at predetermined intervals, the subject's current drift velocity. At step 130, the system may compare the current drift velocity and other recorded subject parameters to the data model to determine whether a deviation from or conformance to the data model indicates the subject is lying. In one embodiment, when the subject is lying the recorded subject parameters may deviate from the data model's bio-signature of a truthful answer. In another embodiment, when the subject is lying the recorded subject parameters may conform to the data model's bio-signature of a false answer. Deviation or conformance may be calculated within any suitable paradigm. Examples include, without limitation: ratio or percentage by which the current drift velocity exceeds the subject's or the data model's threshold-normal drift velocity; ratio or percentage by which the current drift velocity is below or above the threshold-deception drift velocity; comparison of current drift velocity to points on a curve between threshold-normal and threshold-deception values in the data model; and the like. After the comparison (step 130), the system may return to step 120 and continue recording current data. If the comparison warrants, at step 135 the system may alert a user (e.g., the test administrator) that a lie was detected.

The described system and methods may be implemented in any environment and during any task that may subject the subject to conditions that affect eye movements. The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

What is claimed is:

1. A system for detecting deceptive intent of a user, the system comprising:
   a sensing arrangement that collects eye movement data of a user;
   an alerting arrangement that produces a perceptible alert in response to receipt of an alert signal; and
   a control unit in electronic communication with the sensing arrangement and the alerting arrangement, the control unit configured to:
      extract current eye movement dynamics from the eye movement data, the current eye movement dynamics including a current intersaccadic drift velocity of the user,
      compare the current eye movement dynamics to baseline eye movement dynamics, the baseline eye movement dynamics including a threshold drift velocity,
      identify a deceptive intent of the user when the current intersaccadic drift velocity is below the threshold drift velocity by more than a threshold amount, and
      send the alert signal to the alerting arrangement in response to an identification of the deceptive intent.

2. The system of claim 1, wherein the sensing arrangement includes one of a camera and a motion tracking device.

3. The system of claim 1, wherein the sensing arrangement comprises one or more sensors in electronic communication with a computing device of the user.

4. The system of claim 3, wherein the control unit is in electronic communication with the computing device and the alerting arrangement is in electronic communication with a recipient device operated by a recipient of data transmitted by the user, the alerting arrangement being configured to produce the alert on the recipient device.

5. The system of claim 4, wherein the data transmitted by the user is transmitted over a social network to which the computing device of the user and the recipient device are connected.

6. The system of claim 1, wherein the control unit is further configured to calculate the current intersaccadic drift velocity.

7. The system of claim 1, wherein the sensing arrangement comprises sensors incorporated into one of a mobile phone or a tablet.

8. The system of claim 1, wherein control unit is further configured to calculate the threshold drift velocity based on previous eye movement data of the user collected during a calibration process.

9. The system of claim 1, wherein the control unit is further configured to send a remote alert signal to a device remote from the user.

10. A method of determining whether a subject is lying, the method comprising:
    obtaining eye movement data of one or both of the subject's eyes;
    identifying a current intersaccadic drift velocity from the eye movement data;
    comparing, with a control unit, the current intersaccadic drift velocity of the eye movement data to a threshold drift velocity; and
    when the comparison indicates that the current intersaccadic drift velocity is below the threshold drift velocity by more than a threshold amount, corresponding to an indication that the subject is lying, delivering, with the control unit, an alert to a device associated with one or more of the subject and an administrator,
    wherein the threshold drift velocity is part of one or more bio-signatures each corresponding to one of one or more response conditions, wherein one of the one or more response conditions is a deceptive answer to a question.

11. A method of determining whether a subject is lying, the method comprising:
    obtaining baseline eye movement data during one of a known deceptive condition or a known non-deceptive condition;
    calculating a threshold drift velocity from the baseline eye movement data;
    obtaining eye movement data of one or both of the subject's eyes;
    identifying a current intersaccadic drift velocity from the eye movement data;
    comparing, with a control unit, the current intersaccadic drift velocity of the eye movement data to the threshold drift velocity; and
    when the comparison indicates that the current intersaccadic drift velocity is below the threshold drift velocity by more than a threshold amount, corresponding to an indication that the subject is lying, delivering, with the control unit, an alert to a device associated with one or more of the subject and an administrator.

12. The method of claim 11, wherein the baseline eye movement data is obtained from an individual other than the subject.

13. A method of determining whether a subject is lying, the method comprising:
    obtaining eye movement data of one or both of the subject's eyes;
    identifying a current intersaccadic drift velocity from the eye movement data;
    comparing, with a control unit, the current intersaccadic drift velocity of the eye movement data to a threshold drift velocity; and
    when the comparison indicates that the current intersaccadic drift velocity is below the threshold drift velocity by more than a threshold amount, corresponding to an indication that the subject is lying, delivering, with the control unit, an alert to a device associated with one or more of the subject and an administrator,
    wherein identifying the current intersaccadic drift velocity from the eye movement data includes identifying the current intersaccadic drift velocity when the subject is responding to a question.

* * * * *

UNITED STATES PATENT AND TRADEMARK OFFICE
CERTIFICATE OF CORRECTION

PATENT NO. : 11,759,134 B2
APPLICATION NO. : 16/994403
DATED : September 19, 2023
INVENTOR(S) : Stephen L. Macknik et al.

Page 1 of 1

It is certified that error appears in the above-identified patent and that said Letters Patent is hereby corrected as shown below:

On the Title Page

Column 1, (73) Assignee: "ARIZONA BOARD OF REGENTS ON BEHALF OF ARIZONA STATE UNIVERSITY DIGNITY HEALTH, Scottsdale, AZ (US)" should be --ARIZONA BOARD OF REGENTS ON BEHALF OF ARIZONA STATE UNIVERSITY, Scottsdale, AZ (US); DIGNITY HEALTH, San Francisco, CA (US)--.

Signed and Sealed this
Twelfth Day of December, 2023

Katherine Kelly Vidal
*Director of the United States Patent and Trademark Office*